(12) United States Patent
Hsu et al.

(10) Patent No.: US 6,908,678 B2
(45) Date of Patent: *Jun. 21, 2005

(54) PLASTIC SLIDES FOR THE FABRICATION OF BIOCHIPS

(75) Inventors: Li-Wei Hsu, Taichung (TW); Su-Chen Chang, Taichung (TW); Jyh-Phen Chen, Taipei (TW); Jeng-Woei Lee, Yung He (TW)

(73) Assignee: Advanced Gene Technology, Corp., Taichung (TW)

( * ) Notice: Subject to any disclaimer, the term of this patent is extended or adjusted under 35 U.S.C. 154(b) by 234 days.

This patent is subject to a terminal disclaimer.

(21) Appl. No.: 10/052,669

(22) Filed: Jan. 18, 2002

(65) Prior Publication Data

US 2003/0138633 A1 Jul. 24, 2003

(51) Int. Cl.[7] .............................................. B32B 27/38
(52) U.S. Cl. ...................... 428/413; 428/412; 428/523; 428/474.4; 435/6; 435/7.1
(58) Field of Search ................... 428/412, 413, 428/523, 474.4; 435/6, 7.1

(56) References Cited

U.S. PATENT DOCUMENTS 5,989,692 A * 11/1999 Brown ....................... 428/215

| | | |
|---|---|---|
| 6,645,719 B2 | 11/2003 | Chang et al. ................... 435/6 |
| 2002/0028506 A1 * | 3/2002 | Ho et al. .................. 435/305.1 |
| 2002/0127565 A1 * | 9/2002 | Cummingham et al. ........ 435/6 |
| 2003/0113792 A1 * | 6/2003 | Swan et al. ................... 435/7.1 |
| 2003/0190756 A1 | 10/2003 | Hsu et al. .................... 436/161 |
| 2004/0043478 A1 | 3/2004 | Hsu et al. ................. 435/287.2 |

FOREIGN PATENT DOCUMENTS

| EP | 1 026 259 | 2/2000 |
|---|---|---|
| WO | WO 00/36145 | 6/2000 |
| WO | WO 00/55627 | 9/2000 |

* cited by examiner

Primary Examiner—James J. Seidleck
Assistant Examiner—Melanie Bissett
(74) Attorney, Agent, or Firm—Morrison & Foerster LLP

(57) ABSTRACT

The present invention discloses a chemically surface-treated plastic slide that is useful for the immobilization of proteins, peptides or small molecules to its surface for the fabrication of biochips. Also disclosed in the present invention is a surface-treated plastic slide made of polystyrene, which is useful for the immobilization of oligonucleotides or polynucleotides to its treated surface for the fabrication of DNA chips.

16 Claims, 6 Drawing Sheets

1. B-G
2. Biotin
3. BACH
4. BACHSE
5. B-WGA (a)

(b)

PLASTIC SLIDES FOR THE FABRICATION OF BIOCHIPS

TECHNICAL FIELD

The present invention relates to surface-treated plastic slides for use in the fabrication of biochips. In particular, the present invention discloses chemical modification of the surface of a plastic slide for preparing a surface-treated plastic slide, on which microarrays of biological samples can be spotted for the fabrication of biochips.

BACKGROUND ART

Glass slide has been conventionally used in the art as a substrate for the fabrication of DNA chips and protein chips. It has been noted, however, that glass slide has several disadvantages as a substrate of biochips. Firstly, glass slide itself is fragile and has to be handled carefully. It is not easy to chemically modify the surface of glass slide in order to successfully immobilize biological, small molecules (such as metabolites from plants or herbs) to said modified surface for binding directly. Glass slide may produce an undesired, high background signal that interferes with the analysis of the biochips that are sequentially treated with a label. There has been a demand in the art to create a new material or develop a material that could be easily modified in replace of glass as a biochip substrate.

Recently, an effort in the development of a plastic slide-based biochip has been made, based on the ground that a plastic slide is not only more effective in cost than a glass slide, but also can be easily molded into a shape as desired by a conventional injection moulding process.

WO 00/55627 disclosed a biochip for the detection of target analytes, comprising an array of biologically binding ligands immobilized to a non-fluorescent acrylic support.

WO 00/36145 disclosed a method for making a biochip, comprising grafting biological probes on a conductive polymer.

EP 1 026 259 disclosed a DNA chip comprising a solid carrier and oligonucleotides or polynucleotides fixed on the solid carrier in the presence of a hydrophilic polymer.

Though a plastic substrate has been used for the fabrication of DNA chips, however up to date it has not been successful in the art to use a plastic slide, with its surface having been chemically modified, for immobilizing proteins, peptides or small molecules to its treated surface, preferably in microarrays, especially at a condition that those proteins, peptides or small molecules have not been modified.

In addition, there was no teaching or suggestion in the art that a plastic slide made of polystyrene could be treated in one step on its surface with a simple reagent, whereby oligonucleotides or polynucleotides could be immobilized, preferably in microarrays, to its treated surface.

DISCLOSURE OF THE INVENTION

The present invention discloses a chemically surface-treated plastic slide that is useful for the immobilization of proteins, peptides or small molecules to its surface for the fabrication of biochips.

The present invention also discloses a surface-treated plastic slide made of polystyrene, which is useful for the immobilization of oligonucleotides or polynucleotides to its treated surface for the fabrication of DNA chips.

MODES OF CARRYING OUT THE INVENTION

Figure 1A:
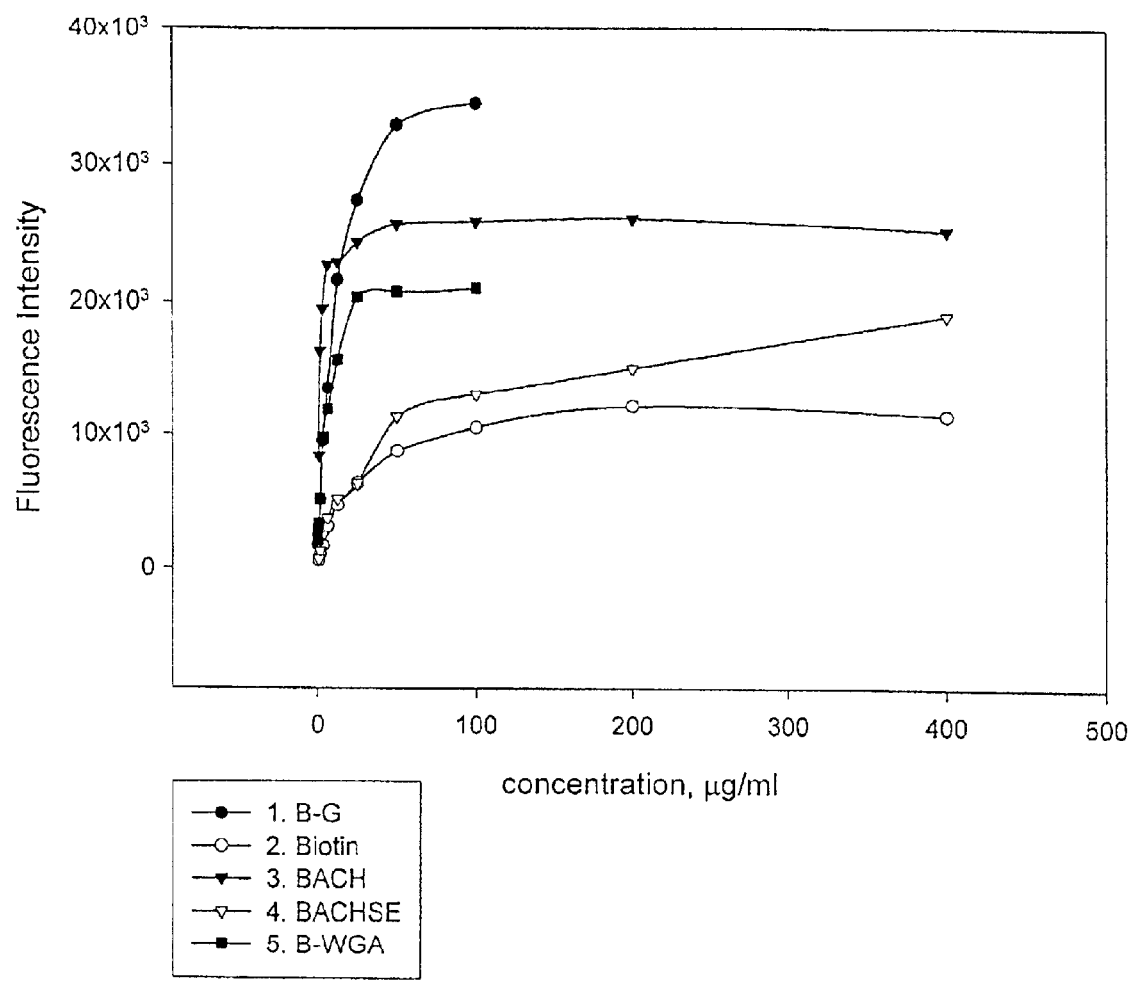
FIG. 1(a) shows fluorescence intensity of the immobilized biotin, biotinylated derivatives and biotinylated protein, which have been probed with Cy-5 labeled streptavidin.
Figure 1A:
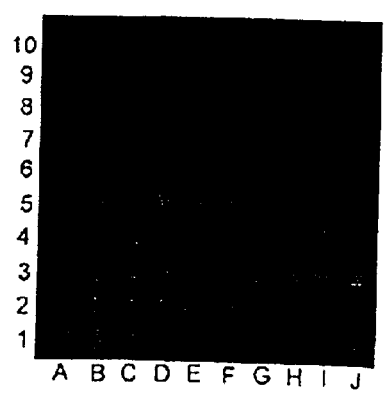

The present invention discloses a chemically surface-treated plastic slide that is useful for the direct immobilization of proteins, peptides or small molecules to its treated surface for the fabrication of biochips. The biochips made of the chemically surface-treated plastic slide of the present invention can be used as a platform for shotgun screening for biologically active ingredients in a target-directed manner for achieving a high throughput.

The material of the plastic slide used in the present invention may be a homopolymer or copolymer, which is made of one or more monomers selected from the group consisting of ethylene, haloethylene, propylene, halopropylene, acrylate, methacrylate, butadiene, acrylonitrile, norbornene and styrene, wherein a polymer of styrene is preferred. Also included in the material of the plastic slide of the present invention is polycarbonate. The plastic slide is comparable in size to the ones conventionally used in the art within a microarrayer and a laser scanner.

The advantage of using a plastic slide in the present invention resides in that there exist a variety of chemicals that can be used for modifying or treating the surface of a plastic slide, whereby not only macromolecules (such as proteins and DNA) but also small molecules (such as metabolites from plants or herbs) can be immobilized to the surface of the plastic slide. Further, the plastic slide of the present invention can be molded in a way to contain preferably at least two cavity chambers, whereby at least two different chemical reactions can be processed simultaneously in said cavity chambers on the same plastic slide. The depth of the cavity chambers may be the same or different, and ranges from less than 0.03 mm to up to 0.5 mm. There may be two bars respectively molded at the opposite sides of each chamber for supporting a glass lid, in order that the glass lid is useful for preventing the evaporation or loss of the solution, with which the chamber is loaded.

In the preparation of the chemically surface-treated plastic slide of the present invention, the raw plastic slide as mentioned above may be pretreated with a polyfunctional aldehyde followed by soaking in a solution of $NH_2$ group (s)-providing precursor, whereby the pretreated plastic slide contains active amino groups on its surface. The $NH_2$ group(s)-providing precursor may be organic or inorganic, and may be selected from the group consisting of $NH_4OH$, primary amine, secondary amine and tertiary amine, wherein the aliphatic or aromatic part of the primary amine, secondary amine and tertiary amine may be useful as an additional spacer arm. Among the $NH_2$ group(s)-providing precursors, $NH_4OH$ and the primary amine that directly provide a free $NH_2$ group are preferred.

The pretreated plastic slide is further coated with a layer of a polyfunctional molecule (e.g. a polyfunctional epoxide) that is useful as a spacer for producing the chemically surface-treated plastic slide of the present invention. In function, the polyfunctional epoxide will act for linking the desired components in test samples spotted on the chemically surface-treated plastic slide, preferably in microarrays. The active epoxy groups on one end of the polyfunctional epoxide react with the amino groups on the surface of the pretreated plastic slide, while the active epoxy groups on the other end of the polyfunctional epoxide react with or absorb the desired components in the test samples. In particular, those components in the test samples that contain free hydroxyl, sulfhydryl or amino groups can form a covalent bond with the active epoxy groups on the other end of the polyfunctional epoxides, and consequently are attached to the chemically surface-treated plastic slide. The polyfunctional epoxides preferably contain a long chemical chain of 6 to 24 carbon atoms, whereby the desired components would not directly bind to the pretreated plastic slide. The binding of the desired components to the chemically surface-treated plastic slide of the present invention is persistent, even after stringent stripping. In the present invention, not only macromolecules (such as proteins and polypeptides) but also small molecules (such as metabolites from plants or herbs), regardless of being homogeneous or heterogeneous, can be immobilized to the surface of the chemically surface-treated plastic slide of the present invention.

Based on the above, the preparation of the chemically surface-treated plastic slide of the present invention comprises the steps of preparing a raw plastic slide preferably provided with cavity chambers, pretreating the raw plastic slide with a polyfunctional aldehyde followed by soaking in a solution of $NH_2$ group(s)-providing precursor (preferably, aqueous ammonia), and coating the surface of the pretreated plastic slide with a polyfunctional molecule (preferably, a polyfunctional epoxide).

The chemically surface-treated plastic slide of the present invention is useful for the preparation of biochips, wherein microarrays of spots containing homogeneous or heterogeneous samples can be immobilized to the surface of the chemically surface-treated plastic slide of the present invention. The biochips thus obtained can be used for the screening for the desired components contained in the spotted test samples based on a target-directed strategy. Such screening may comprise the steps of loading a labeled probe(s)-containing solution onto the biochips for conducting a chemical reaction (wherein each of the chambers may be covered by a glass lid for preventing the evaporation of the labeled probe(s)-containing solution), and imaging and identifying the spots that react with or bind to the labeled probe with an apparatus, e.g. a laser scanner. The label within the probes may be a dye or a radioactive material. Further, the probes used for the hybridization may be homogeneous or heterogeneous, known targets based on a defined molecular mechanism, which may be, for example, small molecules, competitive ligands, or antibodies against, for example, the desired receptors, enzymes, or proteins.

The present invention also discloses a surface-treated plastic slide made of polystyrene for the immobilization of oligonucleotides or polynucleotides to its treated surface, preferably in microarrays, for the fabrication of DNA chips. The DNA chips made of the surface-treated polystyrene slide of the present invention are useful as a platform for the detection of the presence of desired DNAs in the sample spots on its treated surface under hybridization conditions with a labeled probe.

The polystyrene slide used in the present invention may also have a size comparable to the ones conventionally used in the art within a microarrayer and a laser scanner. The polystyrene slide may be also molded in a way to contain preferably at least two cavity chambers as mentioned above, whereby at least two different hybridization reactions can be processed simultaneously in said cavity chambers on the same polystyrene slide. The depth of the cavity chambers may be the same or different, and ranges from less than 0.03 mm to up to 0.5 mm. There may be also two bars respectively molded at the opposite sides of each chamber for supporting a glass lid, in order that the glass lid is useful for preventing the evaporation or loss of the solution, with which the chamber is loaded.

In the modification of the surface of a polystyrene slide, a raw polystyrene slide is coated with a reagent comprising a $NH_4^+$ group-free buffer containing positive charges-providing polymers (e.g. polylysine) under a stronger alkaline condition. The $NH_4^+$ group-free buffer may be a carbonate, phosphate or citrate buffer. The stronger alkaline condition may be at a pH in the range of pH 9 to 11. The advantage in the preparation of the surface-treated polystyrene slide of the present invention resides in that a simple reagent in just one coating step is needed.

The DNA chips thus obtained can be used for the detection of the presence of desired DNAs in the spotted test samples under hybridization conditions with a labeled probe. Such detection method may comprise the steps of loading a labeled probe(s)-containing solution onto the DNA chips for conducting a hybridization reaction (wherein each of the chambers may be covered by a glass lid for preventing the evaporation of the labeled probe(s)-containing solution), and imaging and identifying the spots that bind to the labeled probe(s) with an apparatus, e.g. a laser scanner. Also as mentioned above, the label within the probe(s) may be a dye or a radioactive material.

In effect, both of the biochips and DNA chips made of the surface-treated plastic slide of the present invention show a much weaker fluorescence background than those biochips made of a glass slide.

The following examples are intended to illustrate but not to limit the invention.

EXAMPLE 1

Chemical Modification of the Surface of Polystyrene Slides for Binding Proteins Peptides or Small Molecules Polystyrene slides having a size comparable to that of regular glass slides used in a microscope or laser scanner and having two cavity chambers were used, wherein the depth of each of the cavity chambers is 0.05 mm. The polystyrene slides were washed with double-distilled water, followed by washing with 95% ethanol (EtOH) at room temperature for at least 2 hours. The cleaned polystyrene slides were further washed with double-distilled water for 3 times and were then dried. The resultant polystyrene slides were immersed in a 0.4% glutaldehyde solution in 0.1 M phosphate buffer, pH 5.0 at room temperature for 4 hours, followed by washing with double-distilled water, and then soaking in 3M $NH_4OH$ (pH 11.0) at 60° C. for 4 hours. The resultant polystyrene slides were then treated with 100 mM 1,4-butanediol diglycidyl ether, pH 11.0 at 37° C. overnight. The treated polystyrene slides were washed with double-distilled water and then were dried. The resultant, treated polystyrene slides were ready for the fabrication of biochips, to which proteins, peptides or small molecules are immobilized.

EXAMPLE 2

Modification of the Surface of Polystyrene Slides for Binding DNAs

Polystyrene slides having two cavity chambers as used in Example 1 were washed with double-distilled water, followed by washing with 95% EtOH at room temperature for at least 2 hours. The cleaned polystyrene slides were further washed with double-distilled water for 3 times and were then dried. The resultant polystyrene slides were soaked in a reagent solution containing 1.12% polylysine (Sigma), 0.03% dimethylsulfoxide (DMSO) in 50 mM carbonate buffer, pH 9.5 at room temperature for 30 min. The treated polystyrene slides were removed and washed with double-distilled water for 4 times, and were then dried in the Laminar Flow. The resultant, treated polystyrene slides were ready for the fabrication of DNA chips.

EXAMPLE 3

Preparation of Biochips for Immobilizing Proteins, Peptides or Small Molecules

The robot, MicroGrid II (BioRobotics), having 0.4 mm solid pins was used for arraying proteins, peptides or small molecule samples on the treated polystyrene slides prepared in Example 1. The proteins were dissolved in an aqueous buffer, and the peptides and small molecules were respectively dissolved in DMSO for forming stocks, and then the protein-, peptide- and small molecule-containing stocks were diluted into 30% DMSO/0.1M carbonate buffers, pH 9.5 (see the details in the "Results" section as stated below). The solid pins used to deliver and spot the protein-, peptide- or small molecule-containing solutions were washed with double-distilled water for 2 seconds and then with 70% EtOH for 2 seconds, followed by drying under a stream of hot air for 2 seconds before loading each of said samples. Upon completing arraying on the treated polystyrene slides, the resultant biochips were incubated at room temperature for 2 hours and then immersed in 1M ethanolamine to block the remainder unreacted epoxy groups. The biochips thus obtained were subsequently washed with TBST buffer (50 mM Tris.HCl, 0.15M NaCl, 0.05% Tween 20) 3 times, followed by rinsing with double-distilled water 3 times, and then dried at 37° C.

EXAMPLE 4

Preparation and Processing of DNA Chips

The robot, MicroGrid II (BioRobotics), having 0.4 mm solid pins as mentioned above was used for arraying oligonucleotide or polynucleotide samples in 30% DMSO/SSC on the cavity chambers of the treated polystyrene slides prepared in Example 2 for preparing DNA chips, wherein a row of the oligonucleotide and polynucleotide samples had been previously labeled by using the FluoriLink™Cy3™ bifunctional reactive dye (Amersham) before being arrayed onto the treated polystyrene slides.

The cavity chambers of the DNA chips were loaded with a denaturing solution (1.5M NaCl, 0.5M NaOH) and incubated at room temperature for 2 min. The denaturing solution was then removed from the cavity chambers, and the cavity chambers were loaded with a neutralizing solution (1.5M NaCl, 0.5M Tris-HCl, pH 7.2, 1 mM EDTA) and incubated at room temperature for 1 min. The DNA chips were dried in an oven at 37° C. Crosslinking of the arrayed oligonucleotides or polynucleotides was performed by using a Stratalinker UV crosslinker (Stratagene) at 600 (×100) microjoules for 5 min. The DNA chips were washed with double-distilled water for 1 min. for 4 times. The DNA chips were then immersed in 95% EtOH for 1 min., followed by drying in an oven at 37° C. The DNA chips were soaked in a succinic anhydride/sodium borate solution (Fresh preparation: 5 g succinic anhydride was dissolved in 20 ml 1-methyl-2-pyrrolidone, and just before soaking the DNA chips, 330 ml 0.2M sodium borate, pH 8.0 was added) for 15 min. with gentle agitation. The DNA chips were washed in double-distilled water and 95% EtOH as previously described, and then dried.

EXAMPLE 5

Labeling of Proteins or Peptides with Fluorophores

Cy3-labeled strapavidin (SA), rabbit anti-mouse IgG, and Glucocortcoid receptor peptide were prepared by using the FluoriLink™Cy3™ bifunctional reactive dye (Amersham) according to the protocol recommended by the manufacture company. Similarily, Cy5-labeled SA was prepared by using the FluoriLink™Cy5™ bifunctional reactive dye (Amersham) according to the protocol recommended by the manufacture company.

EXAMPLE 6

Labeling of DNAs with Fluorophore

Cy3-labeled DNAs used as a probe were prepared by using the FluoriLink™Cy3-dCTP (Amersham) according to the protocol recommended by the manufacture company.

EXAMPLE 7

Probing the Biochips with Fluorophores-Labeled Proteins or Peptides

A TBST dilution solution (approximately 20 to 25 µl) of the fluorophores-labeled proteins or peptides prepared in Example 5 was applied to the cavity chambers of the biochips prepared in Example 3, and then the resultant biochips were incubated at room temperature for 2 hours, wherein the cavity chambers were covered with 22×22 mm cover glasses. The biochips were rinsed once with TBST and then gently washed with TBST 3 times, followed by washing with double-distilled water for 4 times. The probed biochips were dried at 37° C., and then were scanned by using GenePix400A slide scanner (Axon Instruments) or stored in the darkness at room temperature.

EXAMPLE 8

Probing the DNA Chips with Fluorophores-Labeled DNAs

The cavity chambers of the DNA chips prepared in Example 4 were incubated in a pre-hybridization buffer (25% formamide, 5×SSC, 0.1% SDS and 1% BSA) at 42° C. for 1 hour, wherein the cavity chambers were covered with 22×22 mm cover glasses. The cavity chambers were then washed with double-distilled water and 95% EtOH. The fluorophore-labeled DNAs (0.4 µg/ml) prepared in Example 6 were sequentially 2× diluted with a buffer containing 25% formamide, 5×SSC, 0.1% SDS, 0.5 mg/ml poly-A blocker and 0.5 mg/ml $E.$ $Coli$ or yeast total RNA. After heating at 95° C. for 5 min. and then chilling on ice for 1 min., the fluorophore-labeled DNAs-containing solution (approximately 20 to 25 µl) was then introduced to the cavity chambers. The DNA chips were incubated at a humidity condition for conducting hybridization at 42° C. overnight. The cover glasses were then removed, and the cavity chambers were washed with 2×SSC. The cavity chambers were washed with 0.1×SSC at room temperature for 5 min. The washing procedure as mentioned above was repeated once, and then the cavity chambers were rinsed with double-distilled water for 5 min. for 4 times. The probed DNA chips thus obtained were dried and then scanned in a manner as mentioned above.

EXAMPLE 9

Scanning of the Probed Biochips and DNA Chips

The probed biochips and DNA chips obtained in Examples 8 and 9 were scanned by using GenePix4000A slide scanner (Axon Instruments) and then analyzed by GenePix 3.0 Software, wherein the quantities were computed by the medium of ratios and presented in the accompanying Figures.

Results

Figure 1B:
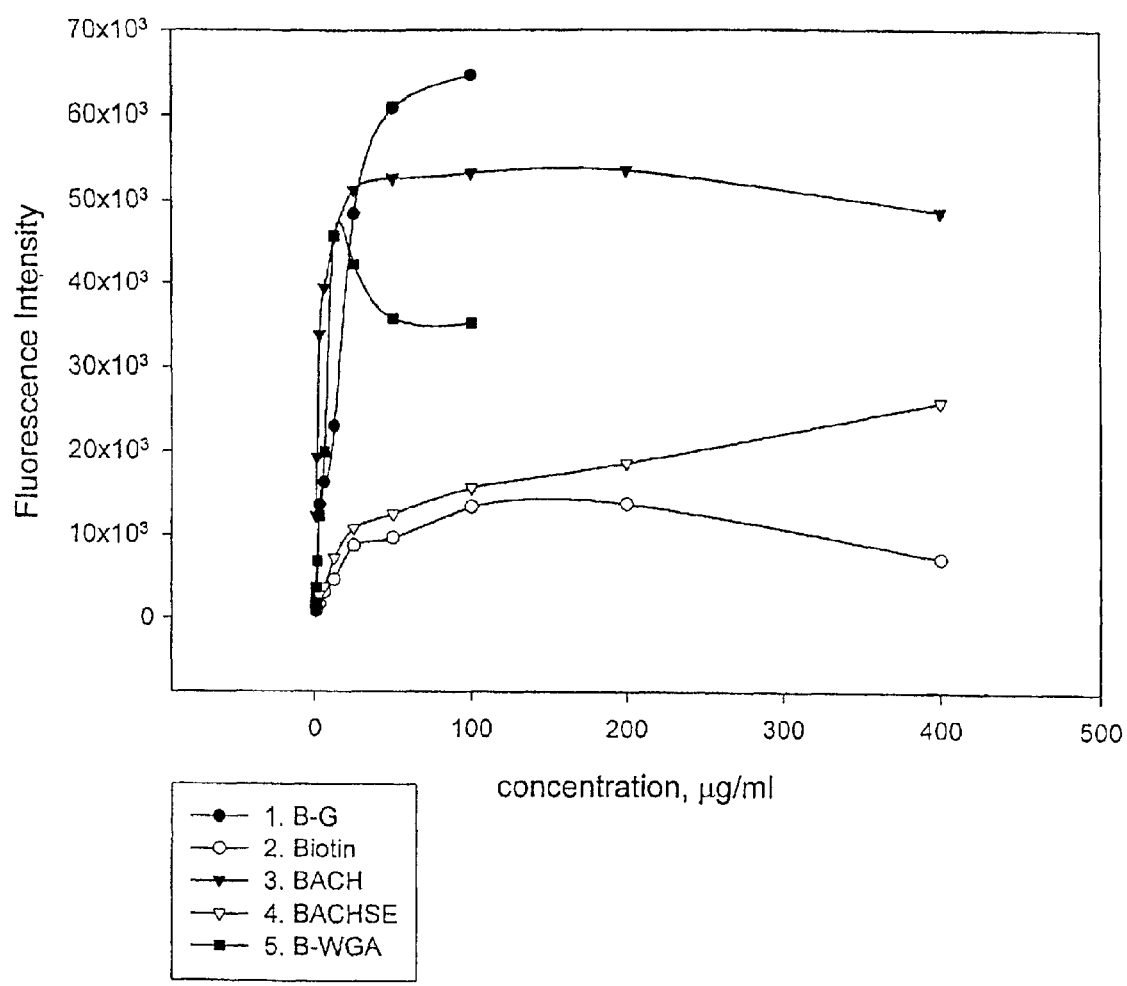
FIG. 1(b) shows fluorescence intensity of the immobilized biotin, biotinylated derivatives and biotinylated protein, which have been probed with Cy-3 labeled streptavidin.
Figure 1B:
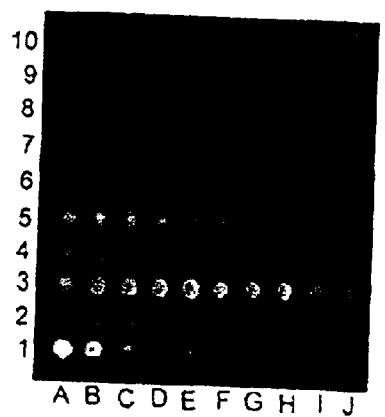
Figure 1:
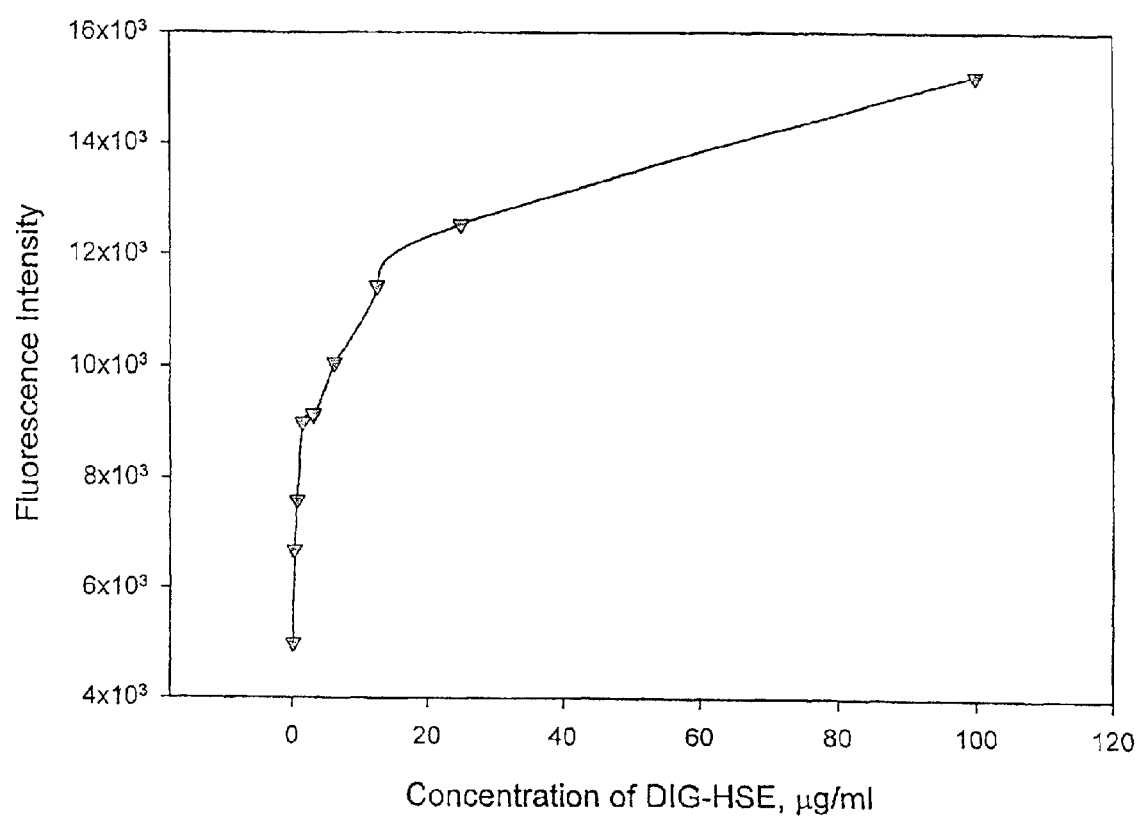
FIG. 1(c) shows fluorescence intensity of immobilized DIG derivative that was hybridized with monoclonal mouse anti-DIG, which was sequentially probed with Cy-3 labeled rabbit anti-mouse IgG.
Figure 1:

Arrayed samples shown in FIGS. 1A, 1B and 1C were serially 2× diluted from Column A to J (left to right). The concentration of each of the first samples in row was as follows:

Row 1. B-G (Biotinylated gelatin), 100 µg/ml

Row 2. Biotin (Sigma B-4501), 400 µg/ml

Row 3. B-ACH (Biotinamidocaproyl hydrazide, Sigma B-3770), 400 µg/ml

Row 4. B-ACHSE (Biotinamidocaproate N-hydroxysuccinimide ester, Sigma B-2643), 400 µg/ml Row 5. B-WGA (Biotinylated wheat germ agglutinin, Vector Lab B1025S), 100 µg/ml Row 6. Human IgG, 100 µg/ml Row 7. DIG-HSE (digoxigenin 3-O-methylcarbonyl-aminocaproic acid-N-hydroxysuccinimide etser, BM 1333054), 100 µg/ml Row 8. Rabbit IgG, 100 µg/ml Row 9. Hydrocortisone, 100 µg/ml Row 10. Peptide PQGIAGQR, 100 µg/ml The concentration of the proteins used in the preparations shown in Figures was as follows:

FIG. 1(a): 1 µg/ml Cy-5 streptavidin

FIG. 1(b): 0.5 µg/ml Cy-3 streptavidin

Figure 2:
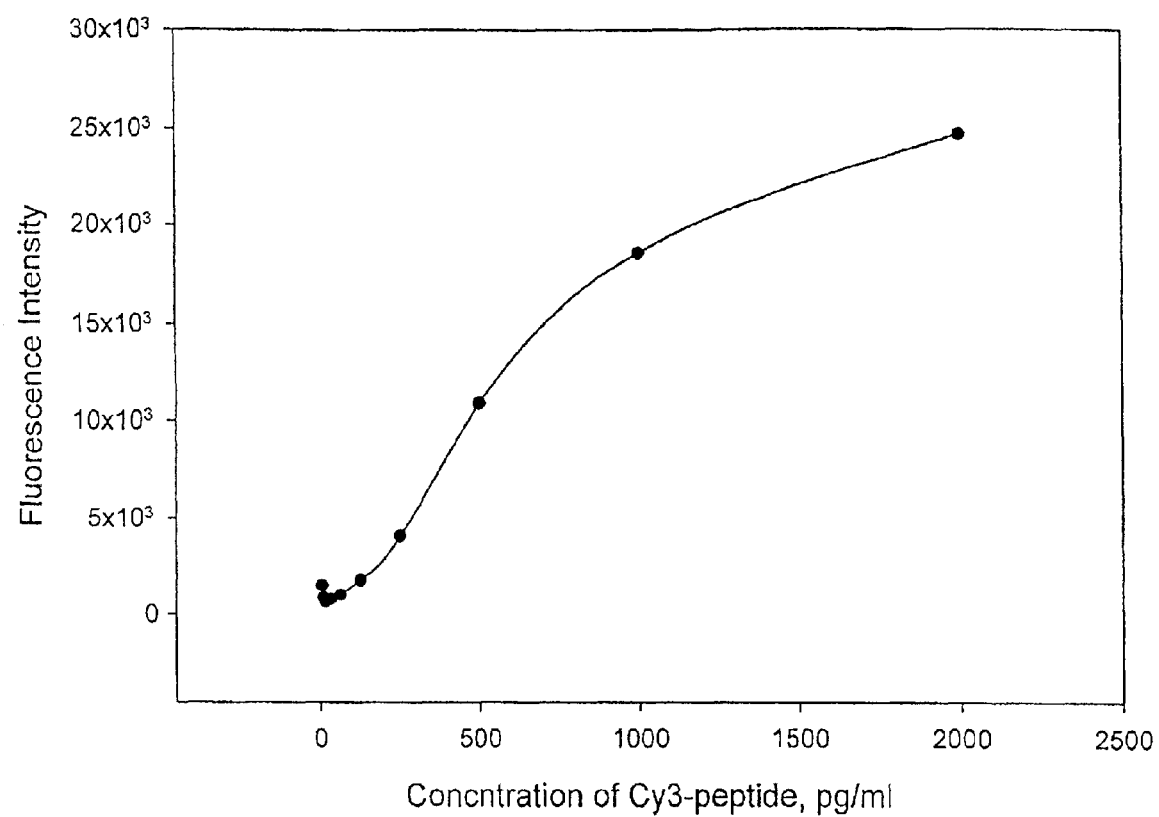
FIG. 2 shows fluorescence intensity of immobilized Cy-3 labeled Glucocortcoid receptor peptide.
Figure 2:

FIG. 1(c): 1/5,000 monocloncal mouse anti-DIG 0.5 µg/ml Cy-3 rabbit anti-mouse IgG The sequence of Cy3-labeled peptide shown in FIG. 2 was CKPLIPDTKPKIKD. The concentration of the arrayed peptides was serially 2× diluted from Column A to J (left to right), beginning with 2 µg/ml.

The DNA used was produced by PCR and purified by the commercial kit (High Pure PCR Product purification kit (BM)) according to the manufacture's instructions.

Figure 3:
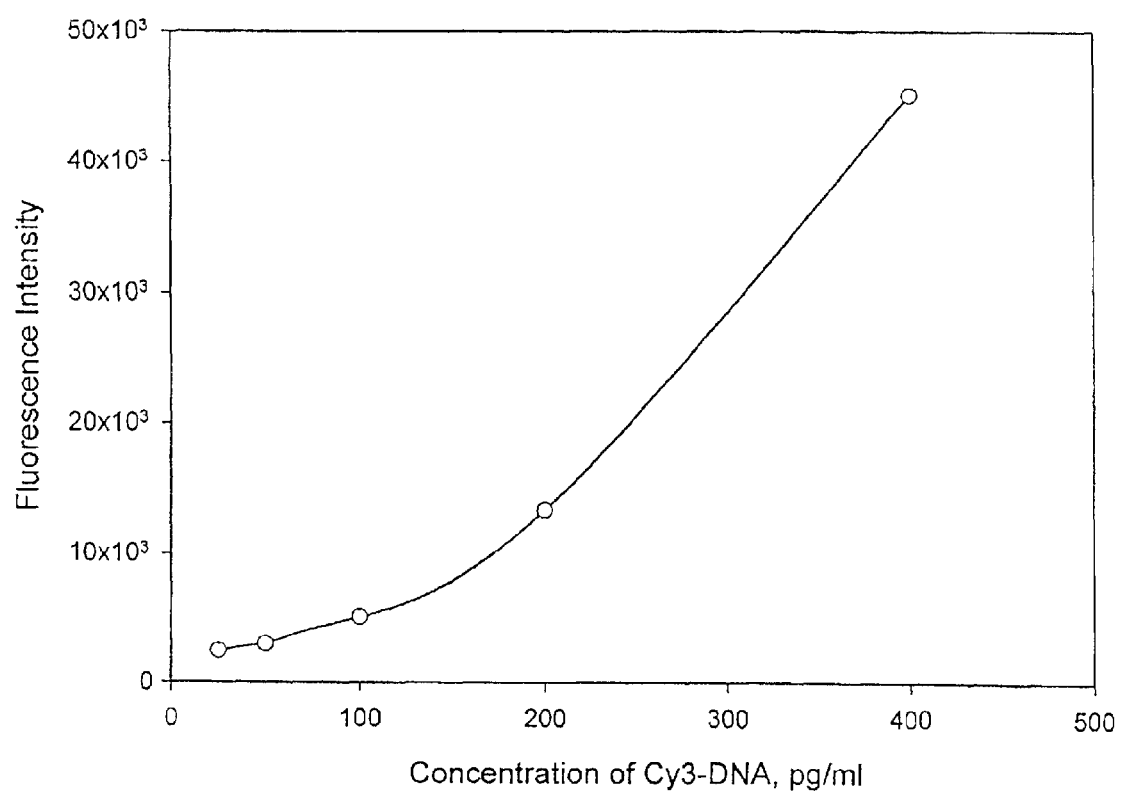
FIG. 3(a) shows fluorescence intensity of immobilized Cy-3 labeled DNA.
FIG. 3(b) shows fluorescence intensity of immobilized DNA that was treated with a Cy-3 labeled DNA probe.
Figure 3:

FIG. 3(a): The Cy-3 labeled DNA, without any modification, was serially diluted for 4 times from A to J in 30% DMSO/SSC. After blocking and washing, the DNA chip was scanned. The first concentration was 0.2 µg/ml.

Figure 3B:
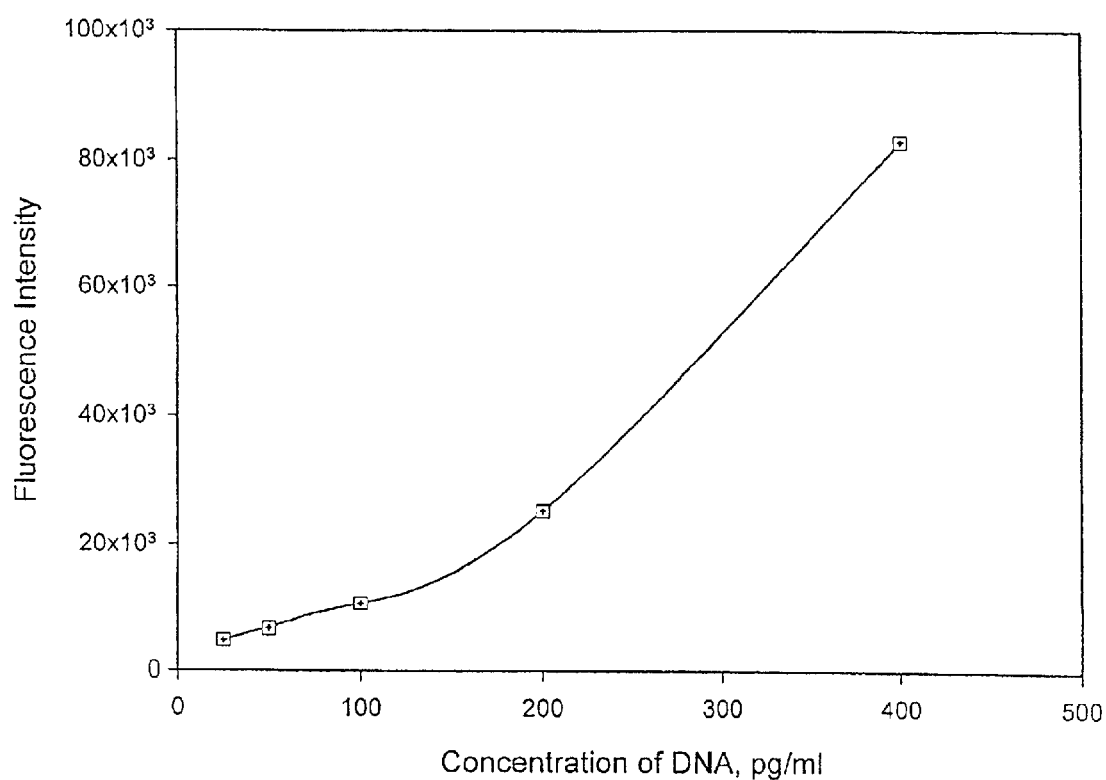
Figure 3B:

FIG. 3(b): The DNA was serially diluted for 4 times from A to J in the buffer as mentioned above. The beginning concentration was 0.4 µg/ml. After blocking and washing, the DNA chip was incubated with Cy-3 labeled DNA probe. The concentration of Cy-3 labeled DNA was 0.1 µg/ml.

What is claimed is:

1. A surface-treated plastic slide comprising a plastic slide and a coating on the plastic slide for immobilizing thereon proteins, peptides or small molecules, wherein said coating comprises a polyfunctional aldehyde coupled to said plastic slide, a compound providing at least one $NH_2$ group which is coupled to said polyfunctional aldehyde, and a polyfunctional epoxide compound comprising at least one epoxy group for coupling to said $NH_2$ group and at least one epoxy group for coupling to said proteins, peptides or small molecules.

2. The surface-treated plastic slide as claimed in claim 1, wherein the plastic slide is formed of a material, which is a polycarbonate, or a homopolymer or copolymer that is made of one or more monomers selected from the group consisting of ethylene, haloethylene, propylene, halopropylene, acrylate, methacrylate, butadiene, acrylonitrile, norbornene and styrene.

3. The surface-treated plastic slide as claimed in claim 2, wherein the plastic slide is formed of a polymer of styrene.

4. The surface-treated plastic slide as claimed in claim 1, wherein the plastic slide has at least one cavity chamber.

5. The surface-treated plastic slide as claimed in claim 4, wherein the plastic slide has two cavity chambers having the same or different depth ranging from 0.03 mm to 0.5 mm.

6. The surface-treated plastic slide as claimed in claim 1, wherein the polyfunctional aldehyde is glutaldehyde.

7. The surface-treated plastic slide as claimed in claim 1, wherein the compound providing at least one $NH_2$ group is $NH_4OH$.

8. The surface-treated plastic slide as claimed in claim 1, wherein the epoxy group(s) for coupling to said proteins, peptides or small molecules can react with their free hydroxyl, sulfhydryl or amino groups.

9. The surface-treated plastic slide as claimed in claim 1, wherein the polyfunctional epoxide compound contains a long chemical chain of 6 to 24 carbon atoms.

10. The surface-treated plastic slide as claimed in claim 1, wherein the proteins, peptides or small molecules are homogeneous or heterogeneous.

11. The surface-treated polystyrene slide comprising a polystyrene slide and a coating on the polystyrene slide for immobilizing thereon oligonucleotides or polynucleotides, wherein the coating is formed by applying to said polystyrene slide a $NH_4^+$ group-free buffer containing a positive charges-providing polymer at an alkaline condition.

12. The surface-treated polystyrene slide as claimed in claim 11, wherein the positive charges-providing polymer is polylysine.

13. The surface-treated polystyrene slide as claimed in claim 11, wherein the $NH_4^+$ group-free buffer is selected from the group consisting of a carbonate, phosphate and citrate buffer.

14. The surface-treated polystyrene slide as claimed in claim 11, wherein the alkaline condition is in the range of pH 9 to 11.

15. The surface-treated polystyrene slide as claimed in claim 11, wherein the polystyrene slide has at least one cavity chamber.

16. The surface-treated polystyrene slide as claimed in claim 15, wherein the polystyrene slide has two cavity chambers having the same or different depth ranging from 0.03 mm to 0.5 mm.

* * * * *